US007803966B2

(12) United States Patent
Oddos et al.

(10) Patent No.: US 7,803,966 B2
(45) Date of Patent: Sep. 28, 2010

(54) COSMETIC AND PHARMACEUTICAL COMPOSITIONS COMPRISING COMPOUNDS THAT DISPLAY RETINOID LIKE ACTIVITIES

(75) Inventors: Thierry Oddos, Meudon (FR); Otto von Stetten, Aachen (DE); Luc van Hijfte, Barr (FR)

(73) Assignee: Johnson & Johnson Consumer France, S.A.S. (FR)

( * ) Notice: Subject to any disclaimer, the term of this patent is extended or adjusted under 35 U.S.C. 154(b) by 6 days.

(21) Appl. No.: 12/335,782

(22) Filed: Dec. 16, 2008

(65) Prior Publication Data

US 2009/0203654 A1     Aug. 13, 2009

(30) Foreign Application Priority Data

Dec. 21, 2007   (EP)  ................................ 07291588

(51) Int. Cl.
*C07C 229/40* (2006.01)
*C07C 229/46* (2006.01)
*C07C 63/331* (2006.01)

(52) U.S. Cl. ...................................... 562/457; 562/490
(58) Field of Classification Search ........................ None
See application file for complete search history.

(56) References Cited

U.S. PATENT DOCUMENTS 5,108,502 A     4/1992   Pawlowski et al.

FOREIGN PATENT DOCUMENTS

| EP | 0 420 713 A | 9/1990 |
|---|---|---|
| GB | 2 204 053 A | 2/1987 |
| JP | 59 067250 A | 4/1984 |
| JP | 01 172415 A | 7/1989 |
| JP | 05 032587 A | 2/1993 |

OTHER PUBLICATIONS

"Cancer." MedLine Plus. (2009). Accessed Mar. 17, 2009. <http://www.nlm.nih.gov/medlineplus/cancer.html>.*
Golub et al. "Molecular Classification of Cancer: Class Discovery and Class Prediction by Gene Expression Monitoring." Science (1999), vol. 286, 521-537.*
Ivanova et al. "RAR-RXR Selectivity and Biological Activity of New Retinoic Acid Analogues with Heterocyclic or Polycyclic Aromatic Systems." Bioorg. Med. Chem. 10 (2002) pp. 2099-2102.*
Johnson et al. "Relationships between drug activity in NCI preclinical in vitro and in vivo models and early clinical trials." British Journal of Cancer (2001), 84(10), 1424-1431.*
Lala et al. "Role of nitric oxide in tumor progression: Lessons from experimental tumors." Cancer and Metastasis Reviews (1998), 17(1), 91-106.*
Sausville et al. "Contributions of Human Tumor Xenografts to Anticancer Drug Development." Cancer Res. 2006, 66(7), Apr. 1, 2006.*

Yoshitomo Kashiwagi et al: "Polypyrrole-supported graphite felt for Heck reaction in solid phase synthesis"Electrochimica Acta, vol. 52, 2007, pp. 3726-3731, XP002482415.
Chongfeng Pann et al: "An Efficient Method to Synthesize Benzofurans arid Naphthofurans" Synlett, No. 11, 2006, pp. 1657-1662, XP002482416.
Muller J.B.: "Spektroskopische Untersuchungen an Orange I and Orange II" Helvetica Chimica Acta, vol. 35, 1952, pp. 2579-2589, XP002482417.
Bergmann E. et al: "Synthesis of Lipophilic Chemotherapeuticals. Vi. Lipophilic Substitutions in Azo-Dyes" Journal of the American Chemical Society, vol. 63, 1941, pp. 2245-2248, XP002482418.
Smitha, P. et al.: "Synthesis, Characterization, and Hyperpolarizability Measurements of Main-Chain Azobenzene Molecules" Journal of Polymer Science, Part A: Polymer Chemistry, vol. 43, No. 19, 2005, pp. 4455-4468, XP002482419.
Haessner, R. et al: "H-NMR-spektroskopische Untersuchungen zur AzoHydrazon-Tautomerie in substituierten 1-Phenylazo-2-naphtholen" Journal Fur Praktische Chemie, vol. 327, No. 4, 1985, pp. 555-566, XP002482420.
Chao, Y.C. et al: "Carboxy-substituted monoazo dyes for wool-polyester blends" Dyes and Pigments, vol. 44, No. 3, 2000, pp. 209-218, XP002482421.
Dann, 0.: "Kupplungen mit diazotiertem 5-Aminothiphencarbons5ure-(2)- dthylester" Chemische Berichte, vol. 82, 1949, pp. 72-76, XP002482422.
Hibbert F. et al: "Kinetics of Removal of the Hydrogen-bonded Proton from Substituted 1-Phenylazo-2-naphthols by Hydroxide Ion" Journal of the Chemical Society, Perkin Transactions 2. Physical Organic Chemistry, vol. 8, 1986, pp. 1283-1288, XP002482423.
Gupta, P.N. et al: "Polarographic Behaviour of Some Azo Compounds" Journal of the Indian Chemical Society, vol. 62, No. 5, 1985, pp. 363-366, XP002482424.
Hodgson H. H. et al: "The Preparation and Diazotisation of pAminomethylaniline" Journal of the Chemical Society, 1944, pp. 398-400, XP002482425.
Galindo C. et al: "UV/H202 oxidation of azodyes in aqueous media: evidence of a structure-degradability relationship" Dyes and Pigments, vol. 42, 1999, pp. 199-207, XP002482427.
Ivanova D. et al.:"RAR-RXR Selectivity and Biological Activity of New Retinoic Acid analogues with Heterocyclic or Polycyclic Aromatic Systems" Bioorganic & Medicinal Chemistry, vol. 10, 2002, pp. 20992012, XP0024822428.
Database Chemcats Chemical Abstracts Service, Columbus, Ohio, US; XP002482467, Order Number: kasf-088804 & "Aurora Screening library" (Sep. 6, 2007), Aurora Fine Chemicals, REIN1NGHAUSSTRASSE 49 GRAZ, A-8020 Austria.

(Continued)

*Primary Examiner*—Golam M. M. Shameem
*Assistant Examiner*—Alicia L Otton

(57) ABSTRACT

This invention relates to novel compounds that display retinoid like activities, including HB-EGF (Heparin Binding Epidermal Growth Factor) release from keratinocytes, cell proliferation, and epidermal thickening without the irritation potentials, such as release of interleukin 8 and inhibition of terminal differentiation of keratinocytes. This invention also relates to the use of such a compound for both external and non-external applications.

11 Claims, 4 Drawing Sheets

OTHER PUBLICATIONS

European Search Report for corresponding Patent Application No. 07291588.7 dated Jun. 19, 2008.
Database CA [Online] Chemical Abstracts Service, Columbus, Ohio, US; Neri, Alberto: "Monosulfonic derivatives of 2- N-phony1-1,2-naphtho-1,2,3-triazole" XP002482430 retrieved from STN Database accession No. 1930:2945 on May 19, 2008.
Database CA [Online] Chemical Abstracts Service, Columbus, Ohio, US; Crippa, G. B. Et Al: "Metallic complexes in the series of a-amino and o-hydroxyazo derivatives" XP002482431 retrieved from STN Database accession No. 1929:29296 on May 19, 2008.
Database Beilstein Beilstein Institute for Organic Chemistry, Frankfurt-Main, DE; XP002482432 Database accession No. 665827, vol. 52, No. 1. p. 270 (1922).
Database Beilstein Beilstein Institute for Organic Chemistry, Frankfurt-Main, DD; XP002482433 Database accession No. 918700, vol. 45, p. 2087 (1912).
Database Beilstein Beilstein Institute for Organic Chemistry, Frankfurt-Main, DE; XP002482435 Database accession No. 922520, pp. 3962-3967 (1969).
Database Beilstein Beilstein Institute for Organic Chemistry, Frankfurt-Main, DE; XP002482436 Database accession No. 750103, vol. 52, No. 1, p. 270 (1922).
Database Beilstein Beilstein Institute for Organic Chemistry, Frankfurt-Main, DE; XP002482437 Database accession No. 4527560, pp. 922-930 (1980).
Database Beilstein Beilstein Institute for Organic Chemistry, Frankfurt-Main, DE; XP002482438, vol. 20, No. 12, pp. 439-440 (1980).
Database Beilstein Beilstein Institute for Organic Chemistry, Frankfurt-Main, DE; XP002482439 Database accession No. 3533672, vol. 6, pp. 849-855 (1951).
Database Beilstein Beilstein Institute for Organic Chemistry, Frankfurt-Main, DE; XP002482440 Database accession No. 3457534, vol. 286, pp. 235-240 (1950).
Database Beilstein Beilstein Institute for Organic Chemistry, Frankfurt-Main, DE; XP002482441 Database accession No. 9199912, vol. 70, pp. 1261-1267 (1987).
Database Beilstein Beilstein Institute for Organic Chemistry, Frankfurt-Main, DE; XP002482442 Database accession No. 8456706, vol. 36, No. 11, pp. 938-944 (1997).
Database Beilstein Beilstein Institute for Organic Chemistry, Frankfurt-Main, DE; XP002482448 Database accession No. 931433, vol. 33, p. 2342 (1960).
Database Beilstein Beilstein Institute for Organic Chemistry, Frankfurt-Main, DE; XP002482448 Database accession No. 748677, vol. 227. p. 1371 (1948).
Database Beilstein Beilstein Institute for Organic Chemistry, Frankfurt-Main, DE; XP002482450 Database accession No. 3277298, vol. 41, No. 10, pp. 1853-1855 (1993).
Database Beilstein Beilstein Institute for Organic Chemistry, Frankfurt-Main, DE; XP002482452 Database accession No. 2332010, vol. 94, pp. 2002-2010 (1961).
Database Beilstein Beilstein Institute for Organic Chemistry, Frankfurt-Main, DE; XP002482453 Database accession No. 2616432 vol. 94, pp. 2002-2010 (1961).
Database Beilstein Beilstein Institute for Organic Chemistry, Frankfurt-Main, DE; XP002482454 Database accession No. 2975503; vol. 43, No. 1 (1969).
Danneberg P. : "Ober fistrushemmende Subskanzen" Zeitschrift Fur Naturforschung, vol. 7b, pp. 468.-474, (1952) XP002482429.
Database Beilstein Beilstein Institute for Organic Chemistry, Frankfurt-Main, DE; XP002482443 Database accession No. 3367918, vol. 52, No. 1, p. 270 (1923).
Database Beilstein Beilstein Institute for Organic Chemistry, Frankfurt-Main, DE; XP002482444 Database accession No. 3394253, vol. 52, No. 1, p. 270 (1922).
Database Beilstein Beilstein Institute for Organic Chemistry, Frankfurt-Main, DE; XP002482445 Database accession No. 659658 vo. 31, pp. 2571-2580 (1966).
Database Beilstein Beilstein Institute for Organic Chemistry, Frankfurt-Main, DE; XP002482446 Database accession No. 665119, vo. 31, pp. 2571-2580 (1966).

* cited by examiner

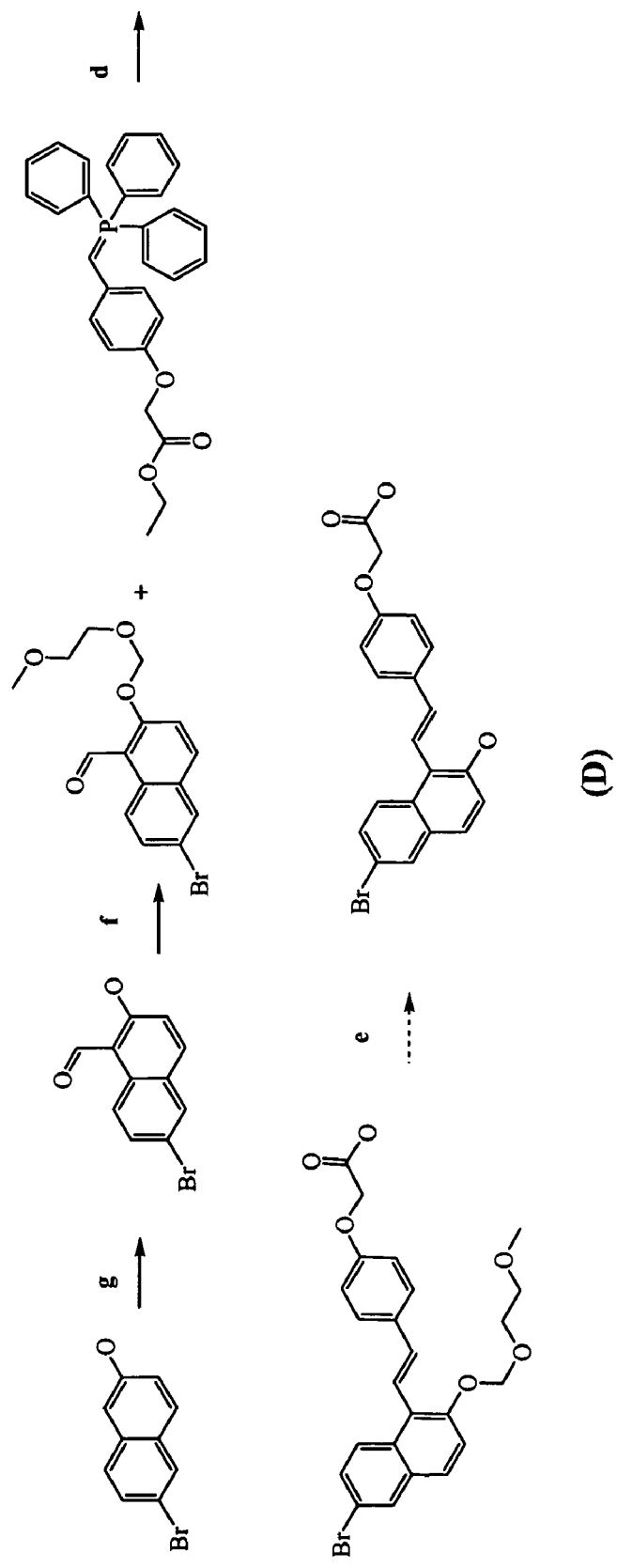
FIG. 1 Synthetic chemical pathways of Compound D
a) BrCH$_2$COOEt, EtONa, EtOH; b) NBS, CHCl$_3$, reflux, 2.5 h; c) toluene, PPh$_3$, reflux, 8h; d) (i) MeONa, EtOH or (ii) NaH, THF; e) HCl, dioxane, water; f) MEM-Cl, DCM, DIPEA, RT; g) (ClCH$_2$)$_2$O, SnCl$_4$

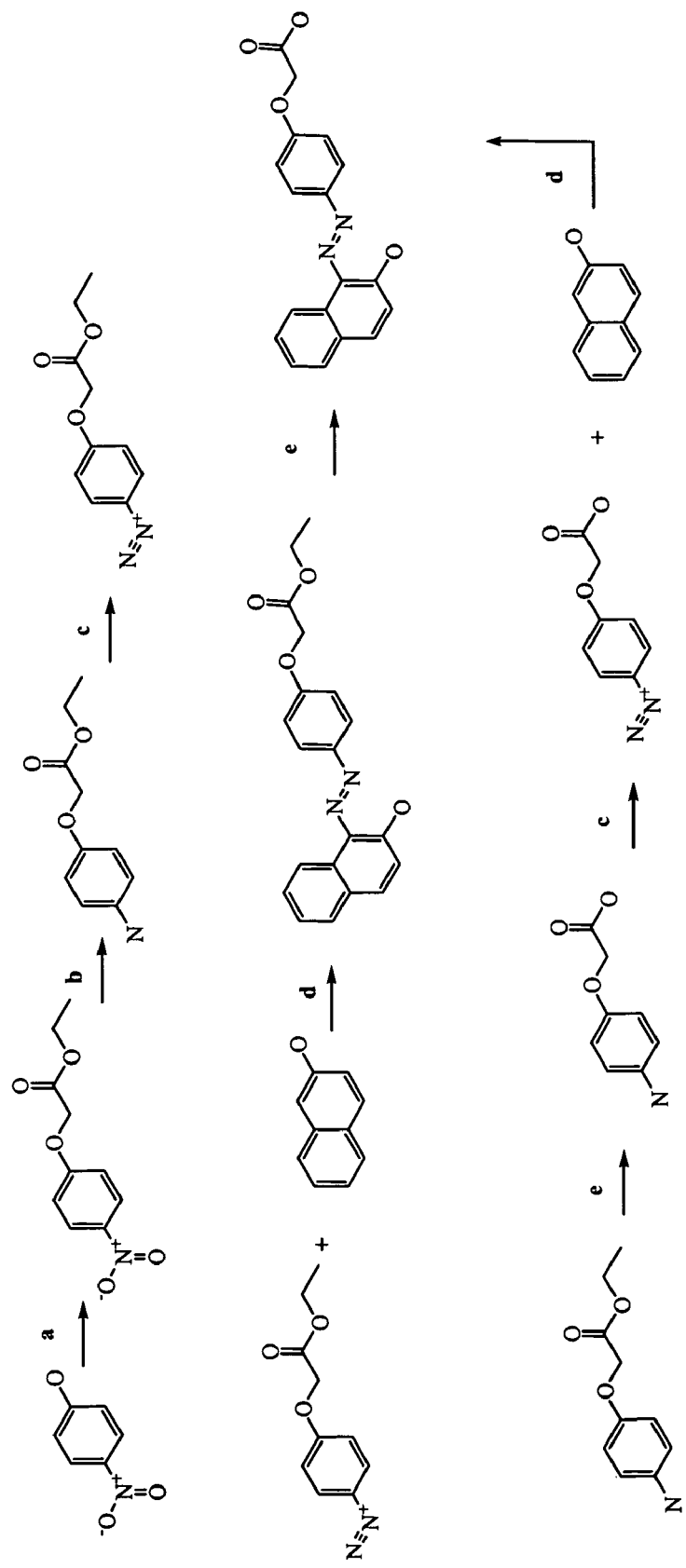
FIG. 2 Synthetic chemical pathways of Compound E
a) BrCH$_2$COOEt, EtONa, EtOH; b) NBS, CHCl$_3$, reflux, 2.5 h; c) toluene, PPh$_3$, reflux, 8h; d) (i) MeONa, EtOH or (ii) NaH, THF; e) HCl, dioxane, water; f) MEM-Cl, DCM, DIPEA, RT; g) (ClCH$_2$)$_2$O, SnCl$_4$

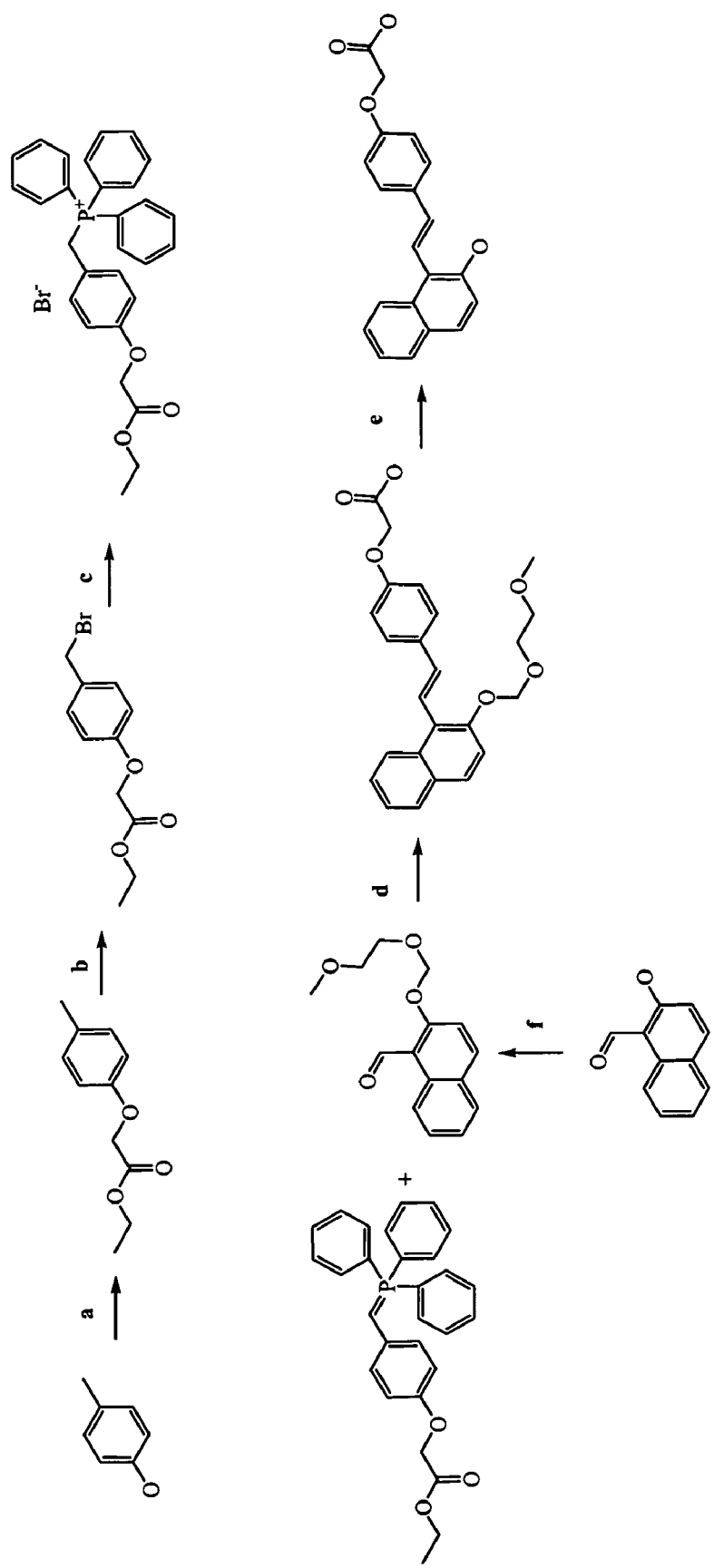
FIG. 3 Synthetic chemical pathways of Compound F
a) BrCH$_2$COOEt, DMF, K$_2$CO$_3$, 60°C; b) H$_2$/Pd, EtOH; c) HCl, NaNO$_2$; d) NaOH; e) KOH, EtOH, H$_2$O, reflux;

Figure 4. Vehicle treated with Compound G after 5 days of treatment
After 5 days of treatment
Control

COSMETIC AND PHARMACEUTICAL COMPOSITIONS COMPRISING COMPOUNDS THAT DISPLAY RETINOID LIKE ACTIVITIES

BACKGROUND OF THE INVENTION

The human skin is subject to certain aging processes, some of which are attributable to intrinsic processes (e.g. chrono-aging) and some of which are attributable to exogenous factors (e.g. photo-aging). In addition, temporary or even lasting changes to the skin can occur, such as acne, greasy or dry skin, keratoses, rosacea, light-sensitive, inflammatory, erythematous, and allergic or autoimmune-reactive reactions, such as dermatosis and photodermatosis.

The consequences of the above-mentioned ageing processes can include thinning of the skin, weaker interlacing of epidermis and dermis, and a reduction in the number of cells and the supplying blood vessels. This often results in the formation of fine lines and wrinkles, and pigment defects can occur.

Retinoids have been used for treating skin conditions caused by intrinsic aging, exogenous factors, or skin diseases. However, despite the beneficial effects of retinoid treatment, its benefits are limited due to skin irritation of retinoids. These side effects can restrict the use of retinoids.

To date, the search for alternative compounds to replace retinoids has produced limited success in treating skin conditions associated with aging, such as skin atrophy, acne, photo-aging, and in reducing the appearance of wrinkles, fine lines, stretch marks, or cellulite.

It is therefore an objective of this invention to provide novel compositions and methods for the treatment of above-mentioned skin conditions that avoid the adverse effects of retinoid administration.

SUMMARY OF THE INVENTION

This invention relates to novel compounds that display retinoid like activities, e.g. in the skin, including HB-EGF (Heparin Binding Epidermal Growth Factor) release from keratinocytes, cell proliferation, and epidermal thickening without the irritation potentials, such as release of interleukin 8 and inhibition of terminal differentiation of keratinocytes.

This invention is directed to a compound of Formula (I)

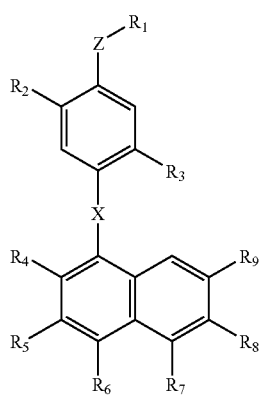

(I)

or cosmetically or pharmaceutically acceptable salts thereof, and compositions containing a compound of Formula I or cosmetically and pharmaceutically acceptable salts thereof, wherein $R_1$ is selected from the group consisting of $COOR_{10}$, $C(=O)R_{11}$, $CH_2OR_{12}$, $SO_2$—OH, —$SO_3$—OH, —$NR_{15}R_{16}$, —$C(=O)$—$NR_{15}R_{16}$, and —$B(OR_{17})_2$;

Z is selected from a bond, oxygen, O—$C_{1-4}$alkyl, $C_{1-4}$alkyl-O—$C_{1-4}$alkyl, O—$C_{2-4}$alkenyl, and $C_{2-4}$alkenyl-O—$C_{2-4}$alkenyl;

$R_2$ is selected from the group consisting of hydrogen and hydroxyl;

$R_3$ is selected from the group consisting of hydrogen and hydroxyl;

X is selected from the group consisting of —$CR_{13}$=$CR_{13'}$— and —N=N—;

$R_4$ is selected from the group consisting of hydrogen, hydroxy, halo, $OR_{14}$, and —$NR_{15}R_{16}$;

$R_5$ is selected from the group consisting of hydrogen, hydroxy, halo, $OR_{14}$, and —$NR_{15}R_{16}$;

$R_6$ is selected from the group consisting of hydrogen and $C_{1-8}$alkyl;

$R_7$ is selected from the group consisting of hydrogen and $C_{1-8}$alkyl;

$R_8$ is selected from the group consisting of hydrogen, hydroxy, halo, $OR_{14}$, and —$NR_{15}R_{16}$;

$R_9$ is selected from the group consisting of hydrogen, hydroxy, halo, $OR_{14}$, and —$NR_{15}R_{16}$;

$R_{10}$ is selected from the group consisting of hydrogen and $C_{1-8}$alkyl;

$R_{11}$ is selected from the group consisting of hydrogen and $C_{1-8}$alkyl;

$R_{12}$ is selected from the group consisting of hydrogen and $C_{1-8}$alkyl;

$R_{13}$ and $R_{13'}$ each independently are selected from the group consisting of hydrogen and $C_{1-4}$alkyl;

$R_{14}$ is $C_{1-4}$alkyl;

$R_{15}$ and $R_{16}$ are each independently selected from the group consisting of hydrogen and $C_{1-4}$alkyl;

$R_{17}$ is independently selected from the group consisting of hydrogen and $C_{1-4}$alkyl.

This invention also relates to the use of such a compound for both external and non-external applications.

Other features and advantages of this invention will be apparent from the detailed description of this invention and from the claims.

BRIEF DESCRIPTION OF THE FIGURES

FIG. 1 Synthetic chemical pathways of Compound D
FIG. 2 Synthetic chemical pathways of Compound G
FIG. 3 Synthetic chemical pathways of Compound F FIG. 4 Skin explant treated with Compound G after 5 days of treatment

DETAILED DESCRIPTION OF THE INVENTION

It is believed that one skilled in the art can, based upon the description herein, utilize this invention to its fullest extent. The following specific embodiments can be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight of the total composition unless otherwise specified.

The compound of this invention is defined as of Formula I

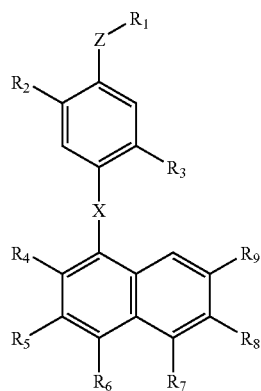

(I)

or cosmetically or pharmaceutically acceptable salts thereof, wherein $R_1$ is selected from the group consisting of $COOR_{10}$, $C(=O)R_{11}$, $CH_2OR_{12}$, $SO_2$—OH, —$SO_3$—OH, —$NR_{15}R_{16}$, —$C(=O)$—$NR_{15}R_{16}$, and —$B(OR_{17})_2$;

Z is selected from a bond, oxygen, O—$C_{1-4}$alkyl, $C_{1-4}$alkyl-O—$C_{1-4}$alkyl, O—$C_{2-4}$alkenyl, and $C_{2-4}$alkenyl-O—$C_{2-4}$alkenyl;

$R_2$ is selected from the group consisting of hydrogen and hydroxyl;

$R_3$ is selected from the group consisting of hydrogen and hydroxyl;

X is selected from the group consisting of —$CR_{13}=CR_{13'}$— and —N=N—;

$R_4$ is selected from the group consisting of hydrogen, hydroxy, halo, $OR_{14}$, and —$NR_{15}R_{16}$;

$R_5$ is selected from the group consisting of hydrogen, hydroxy, halo, $OR_{14}$, and —$NR_{15}R_{16}$;

$R_6$ is selected from the group consisting of hydrogen and $C_{1-8}$alkyl;

$R_7$ is selected from the group consisting of hydrogen and $C_{1-8}$alkyl;

$R_8$ is selected from the group consisting of hydrogen, hydroxy, halo, $OR_{14}$, and —$NR_{15}R_{16}$;

$R_9$ is selected from the group consisting of hydrogen, hydroxy, halo, $OR_{14}$, and —$NR_{15}R_{16}$;

$R_{10}$ is selected from the group consisting of hydrogen and $C_{1-8}$alkyl;

$R_{11}$ is selected from the group consisting of hydrogen and $C_{1-8}$alkyl;

$R_{12}$ is selected from the group consisting of hydrogen and $C_{1-8}$alkyl;

$R_{13}$ and $R_{13'}$ each independently are selected from the group consisting of hydrogen and $C_{1-4}$alkyl;

$R_{14}$ is $C_{1-4}$alkyl;

$R_{15}$ and $R_{16}$ are each independently selected from the group consisting of hydrogen and $C_{1-4}$alkyl;

$R_{17}$ is independently selected from the group consisting of hydrogen and $C_{1-4}$alkyl.

In one embodiment of the present invention the compounds of Formula (I) are those compounds of Formula (I) wherein $R_6$ and $R_7$ are both hydrogen.

In another embodiment of the present invention the compounds of Formula (I) are those compounds of Formula (I) wherein $R_5$ is hydrogen In yet another embodiment of the present invention the compounds of Formula (I) are those compounds of Formula (I) wherein $R_2$ is hydrogen.

Interesting compounds of the formula I are compounds of formula (IA)

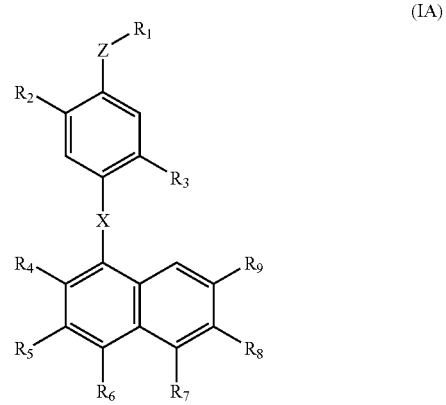

(IA)

wherein $R_1$ is selected from the group consisting of $COOR_{10}$, $C(=O)R_{11}$, $CH_2OR_{12}$;

Z is selected from a bond, oxygen, O—$C_{1-4}$alkyl, $C_{1-4}$alkyl-O—$C_{1-4}$alkyl;

$R_2$ is selected from the group consisting of hydrogen and hydroxy;

$R_3$ is selected from the group consisting of hydrogen and hydroxyl;

X is selected from the group consisting of —$CR_{13}=CR_{13'}$— and —N=N—;

$R_4$ is selected from the group consisting of hydrogen, hydroxy, $OR_{14}$, and —$NR_{15}R_{16}$;

$R_5$ is selected from the group consisting of hydrogen and halo;

$R_6$ is selected from the group consisting of hydrogen and $C_{1-8}$alkyl;

$R_7$ is selected from the group consisting of hydrogen and $C_{1-8}$alkyl;

$R_8$ is selected from the group consisting of hydrogen, hydroxy, halo, $OR_{14}$, and $-NR_{15}R_{16}$;

$R_9$ is selected from the group consisting of hydrogen, hydroxy and $OR_{14}$;

$R_{10}$ is selected from the group consisting of hydrogen and $C_{1-4}$alkyl;

$R_{11}$ is selected from the group consisting of hydrogen and $C_{1-4}$alkyl;

$R_{12}$ is selected from the group consisting of hydrogen and $C_{1-4}$alkyl;

$R_{13}$ and $R_{13'}$ each independently are selected from the group consisting of hydrogen, and $C_{1-4}$alkyl;

$R_{14}$ is $C_{1-4}$alkyl;

$R_{15}$ and $R_{16}$ are each independently selected from the group consisting of hydrogen and $C_{1-4}$alkyl.

Preferred compounds are compounds of formula (IB)

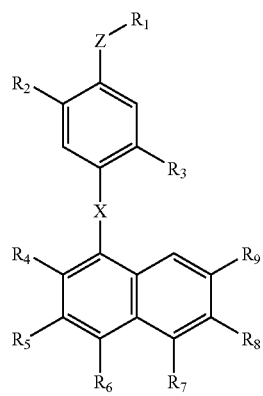

(IB)

wherein:

$R_1$ is $COOR_{10}$,

Z is selected from the group consisting of a bond and $O-C_{1-4}$alkyl, $R_2$ is hydrogen, $R_3$ is hydroxy, X is selected from the group consisting of $-CH=CH-$ and $-N=N-$;

$R_4$ is selected from the group consisting of hydroxy, and $-NR_{15}R_{16}$;

$R_5$ is hydrogen;

$R_6$ is hydrogen;

$R_7$ is hydrogen;

$R_8$ is selected from the group consisting of hydrogen, and halo;

$R_9$ is hydroxy;

$R_{10}$ is hydrogen; and each $R_{15}$ and $R_{16}$ are each independently hydrogen.

Particularly preferred Compounds A-G are selected from the compounds of the formula I:

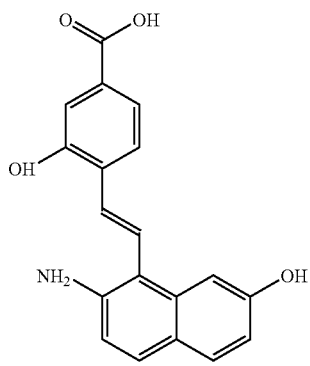

(A)

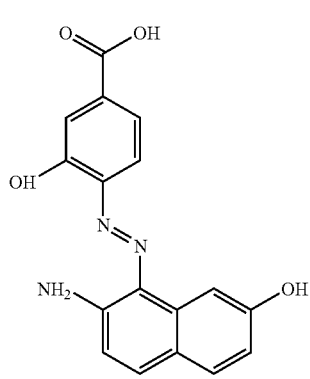

(B)

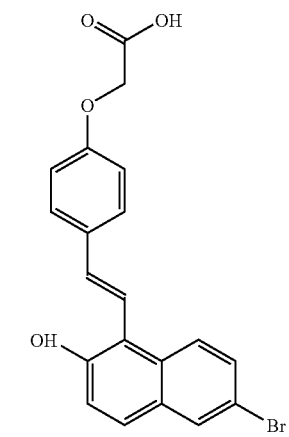

(D)

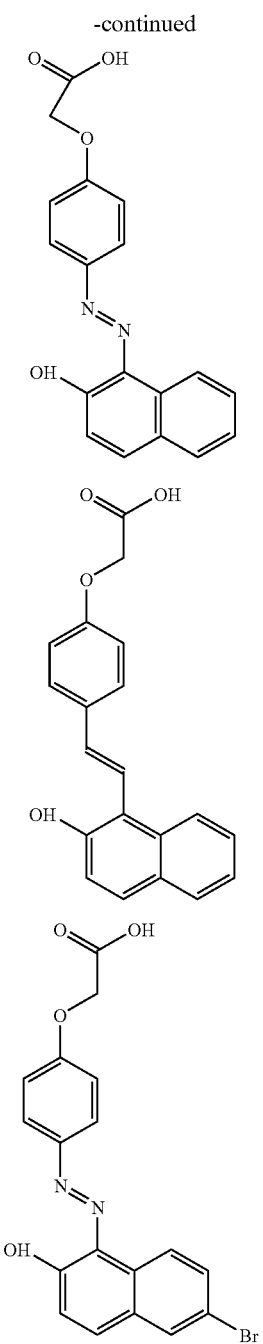

The compound of Formula I of this invention may be prepared using methodology that is well known by a person of ordinary skill. For example, Compounds D, G, and F can be made by the synthetic chemical pathways illustrated in FIGS. 1-3, respectively. The conditions set out here are specific embodiments that can be generalized to any and all of the compounds represented by Formula I.

The compound of Formula I of this invention may also be present in the form of cosmetically or pharmaceutically acceptable salts. For use in cosmetics and pharmaceutics, the salts of the compounds of this invention refer to non-toxic "cosmetically or pharmaceutically acceptable salts", which are cosmetically or pharmaceutically acceptable acidic/anionic or basic/cationic salts. Cosmetically or pharmaceutically acceptable acidic/anionic salts include, but are not limited to, acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Cosmetically-acceptable basic/cationic salts include, and are not limited to aluminum, benzathine, calcium, chloroprocaine, choline, diethanolamine, ethylenediamine, lithium, magnesium, meglumine, potassium, procaine, sodium and zinc. Other salts may, however, be useful in the preparation of compounds according to this invention or of their cosmetically acceptable salts. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p toluenesulfonic, cyclohexanesulfamic, saccharinic or trifluoroacetic acid.

Terms

As used herein, the following terms are intended to have the following definitions. Additional definitions are provided throughout the specification as needed.

The term "$C_{1-8}$ alkyl," whether used alone or as part of a substituent group, refers to a saturated aliphatic branched or straight-chain monovalent hydrocarbon radical having from 1-8 carbon atoms. For example, "$C_{1-8}$alkyl" specifically includes the radicals methyl, ethyl, 1-propyl, 2-propyl, 1-butyl, 2-butyl, tert-butyl, 1-butyl, 1-pentyl, 2-pentyl, 3-pentyl, 1-hexyl, 2-hexyl, 3-hexyl, 1-heptyl, 2-heptyl, 3-heptyl, 1-octyl, 2-octyl, 3-octyl and the like. Said term may also refer to the corresponding alkyldiyl radical. Alkyl and alkyldiyl radicals may be attached to a core molecule via a terminal carbon atom or via a carbon atom within the chain. Similarly, any number of substituent variables may be attached to an alkyl or alkyldiyl radical when allowed by available valences.

The term "$C_{1-4}$alkyl," whether used alone or as part of a substituent group, refers to a saturated aliphatic branched or straight-chain monovalent hydrocarbon radical or alkyldiyl linking group having a specified number of carbon atoms, wherein the radical is derived by the removal of one hydrogen atom from a carbon atom and the alkyldiyl linking group is derived by the removal of one hydrogen atom from each of two carbon atoms in the chain. The term "$C_{1-4}$alkyl" refers to a radical having from 1-4 carbon atoms in a linear or branched arrangement. For example, "$C_{1-4}$alkyl" specifically includes the radicals methyl, ethyl, 1-propyl, 2-propyl, 1-butyl, 2-butyl, tert-butyl, 1-butyl, and the like. Alkyl and alkyldiyl radicals may be attached to a core molecule via a terminal carbon atom or via a carbon atom within the chain. Similarly, any number of substituent variables may be attached to an alkyl or alkyldiyl radical when allowed by available valences.

The term "$C_{2-4}$alkenyl" refers to an alkenyl radical having from 2-4 carbon atoms. For example, specifically includes the radicals ethenyl, propenyl, allyl (2-propenyl), butenyl and the like. As described above, an alkenyl radical may be similarly attached to a core molecule and further substituted where indicated.

The term "halo" as such or in combination with other terms means halogen atom, such as fluoro, chloro, bromo or iodo.

The term "substituted," refers to a core molecule in which one or more hydrogen atoms have been replaced with that amount of substituents allowed by available valences. Substitution is not limited to the core molecule, but may also occur on a substituent radical, whereby the radical becomes a linking group.

The term "independently selected" refers to two or more substituents that may be selected from a substituent variable group, wherein the selected substituents may be the same or different.

The term "dependently selected" refers to one or more substituent variables that are specified in an indicated combination for substitution in a core molecule (e.g. variables that refer to groups of substituents appearing in a tabular list of compounds).

In general, IUPAC nomenclature rules are used herein.

Compositions

The compositions useful in this invention involve formulations suitable for administering to the target tissues, such as human skin. In one embodiment, the composition contains at least a one compound of Formula I and at least one cosmetically or pharmaceutically acceptable carrier.

As used herein, "cosmetically acceptable" means that cosmetically active agents, inert ingredients, or composition which the term describes are suitable for use in contact with tissues (e.g., the skin) without undue toxicity, incompatibility, instability, irritation, allergic response, and the like, commensurate with a reasonable benefit/risk ratio.

As used herein, "pharmaceutically acceptable" means that the ingredient(s) or composition which the term describes are suitable for pharmaceutical administration without undue toxicity, incompatibility, instability, irritation, allergic response, and the like.

The composition according to this invention preferably comprises at least one compound of Formula (I) up to 15% by weight. Preferably the concentration of the compound of Formula (I) is from about here in ratios of from 10% to 0.01% in the composition, and about 5% to about 0.1% being particularly preferred.

The compositions may be made into a wide variety of cosmetic articles that include but are not limited to lotions, creams, gels, sticks, sprays, ointments, cleansing liquid washes and solid bars, shampoos and hair conditioners, pastes, foams, powders, mousses, shaving creams, wipes, strips, patches, electrically-powered patches, wound dressing and adhesive bandages, hydrogels, film-forming products, facial and skin masks, make-up such as foundations, eye liners, and eye shadows, and the like. These product types may contain several types of cosmetically-acceptable carriers including, but not limited to solutions, suspensions, emulsions such as microemulsions and nanoemulsions, gels, solids and liposomes. The following are non-limitative examples of such carriers. Other carriers can be formulated by those of ordinary skill in the art.

The compositions useful in this invention can be formulated as solutions. Solutions typically include an aqueous or organic solvent (e.g., from about 50% to about 99.99% or from about 90% to about 99% of a cosmetically acceptable aqueous or organic solvent). Examples of suitable organic solvents include: propylene glycol, polyethylene glycol (e.g. 200-600), polypropylene glycol (e.g. 425-2025), glycerol, 1,2,4-butanetriol, sorbitol esters, 1,2,6-hexanetriol, ethanol, and mixtures thereof.

A lotion can be made from such a solution. Lotions typically contain from about 1% to about 20% (e.g., from about 5% to about 10%) of an emollient(s) and from about 50% to about 90% (e.g., from about 60% to about 80%) of water. As used herein, "emollients" refer to materials used for the prevention or relief of dryness, as well as for the protection of the skin or hair. Examples of emollients include, but are not limited to, those set forth in the International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., $7^{th}$ Edition, 1997) (hereinafter "ICI Handbook").

Another type of product that may be formulated from a solution is a cream. A cream typically contains from about 5% to about 50% (e.g., from about 10% to about 20%) of an emollient(s) and from about 45% to about 85% (e.g., from about 50% to about 75%) of water.

Yet another type of product that may be formulated from a solution is an ointment. An ointment may contain a simple base of animal, vegetable, or synthetic oils or semi-solid hydrocarbons. An ointment may contain from about 2% to about 10% of an emollient(s) plus from about 0.1% to about 2% of a thickening agent(s). Examples of thickening agents include, but are not limited to, those set forth in the ICI Handbook pp. 1693-1697.

The compositions useful in this invention can also be formulated as emulsions. If the carrier is an emulsion, from about 1% to about 10% (e.g., from about 2% to about 5%) of the carrier contains an emulsifier(s). Emulsifiers may be nonionic, anionic or cationic. Examples of emulsifiers include, but are not limited to, those set forth in the ICI Handbook, pp. 1673-1686.

Lotions and creams can be formulated as emulsions. Typically such lotions contain from 0.5% to about 5% of an emulsifier(s), while such creams would typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the art and are useful in the subject invention. Multiphase emulsion compositions, such as the water-in-oil-in-water type or the oil-in-water-in-oil type, are also useful in the subject invention. In general, such single or multiphase emulsions contain water, emollients, and emulsifiers as essential ingredients.

The compositions of this invention can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contain between about 0.1% and 5%, by weight, of such gelling agents.

The compositions of this invention can also be formulated into a solid formulation (e.g., a wax-based stick, soap bar composition, powder, and wipe containing powder).

The compositions useful in the subject invention may contain, in addition to the aforementioned components, a wide variety of additional oil-soluble materials and/or water-soluble materials conventionally used in compositions for use on skin at their art-established levels.

The compositions of this invention can also be formulated into a ingestible composition. As used herein, "ingestible composition" means a composition that is intended to be ingested. Examples of forms of ingestible compositions include, but are not limited to, tablets, pills, capsules, powders, granules, solutions or suspensions, and drops. Such compositions may be swallowed whole or may be in chewable form. An "ingestible composition" may also be in the form of a confectionary or a food product such as a cookie, candy, food bar, chewing gum, yogurt additive, sprinkles, tea, juice or other drink, liquid shake or the like. Ingestible compositions do not include compositions intended to be topically administered to the skin or oral/vaginal cavity.

Use

The composition according to the invention can be used to treat a variety of skin diseases and conditions, such as reducing the appearance of skin aging, skin inflammation, and skin pigmentation.

Examples of skin aging that may be treated by topical or oral use of the compositions of this invention include, but are not limited to, wrinkles on the skin, loss of the firmness or elasticity of the skin, sagging, lax. As used herein, the term "wrinkle" includes fine line, fine wrinkles, coarse wrinkles, cellulite, scars, and stretch marks. Examples of wrinkles include, but are not limited to, fine lines around the eyes (e.g., "crow's feet"), forehead and cheek wrinkles, frown-lines, and laugh-lines around the mouth.

Examples of skin inflammation that may be treated by topical or oral use of the compositions of this invention include, but are not limited to, arthritis, contact dermatitis, atopic dermatitis, psoriasis, seborrheic dermatitis, eczema, allergic dermatitis, polymorphous light eruptions, inflammatory dermatoses, folliculitis, alopecia, poison ivy, insect bites, irritation induced by extrinsic factors including, but not limited to, chemicals, trauma, pollutants (such as cigarette smoke) and UV or wind exposure, and secondary conditions resulting from inflammation including but not limited to xerosis, hyperkeratosis, pruritus, post-inflammatory hyper-pigmentation, scarring and the like.

Examples of skin pigmentation that may be treated by topical or oral use of the compositions of this invention include, but are not limited to, skin hyper-pigmentation, light areas of the skin, uneven tone of the skin, discoloration and puffiness around the eye. Discoloration and puffiness around the eye include, but are not limited to, dark circles and bags under the eye. In one embodiment, the dark circles under the eye being treated are a result of the increase concentration of blood in the skin under the eye.

Topical Uses

Topical uses of the compositions of this invention containing at least one compound of the Formula (I) and a cosmetically acceptable carrier are for ageing of the human skin, dry skin, pigment defects, UV damages on the skin, skin unevenness, such as wrinkles, fine lines, rough skin or large-pored skin, and diseases associated with skin ageing, such as defective keratinization, acne, eczema, inflammation, and skin atrophy.

As used herein, "topical use" and "topically applying" means directly laying on or spreading on the skin, hair, or nail, e.g., by use of the hands or an applicator such as a wipe.

Additional Cosmetically Active Agents

In one embodiment, the topical composition further includes cosmetically active agent. What is meant by a "cosmetically active agent" is a compound that has a cosmetic or therapeutic effect on the skin, hair, or nails, e.g., lightening agents, darkening agents such as self-tanning agents, anti-acne agents, shine control agents, anti-microbial agents, anti-inflammatory agents, anti-mycotic agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, firming agents, anti-callous agents, and agents for hair, nail, and/or skin conditioning.

In one embodiment, the cosmetically active agent is selected from, but not limited to, the group consisting of hydroxy acids, benzoyl peroxide, sulfur resorcinol, ascorbic acid, D-panthenol, hydroquinone, octyl methoxycinnamate, titanium dioxide, octyl salicylate, homosalate, avobenzone, polyphenolics, carotenoids, free radical scavengers, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, coenzyme Q10, lipoic acid, amino acids such a proline and tyrosine, vitamins, lactobionic acid, acetyl-coenzyme A, niacin, riboflavin, thiamin, ribose, electron transporters such as NADH and FADH2, and other botanical extracts such as aloe vera, feverfew, and soy, and derivatives and mixtures thereof. The cosmetically active agent will typically be present in the composition of the invention in an amount of from about 0.001% to about 20% by weight of the composition, e.g., about 0.01% to about 10% such as about 0.1% to about 5%.

Examples of vitamins include, but are not limited to, vitamin A, vitamin Bs (such as vitamin B3, vitamin B5, and vitamin B12), vitamin C, vitamin K, and vitamin E, and derivatives thereof.

In one embodiment, the composition also contains one or more antioxidants. Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, ascorbic acid, and ascorbic acid derivatives (e.g., ascorbyl palmitate and ascorbyl polypeptide). Oil-soluble antioxidants suitable for use in the compositions of this invention include, but are not limited to, butylated hydroxytoluene, tocopherols (e.g., tocopheryl acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, and propolis. Other examples of antioxidants may be found on pages 1612-13 of the ICI Handbook.

Mineral Water

The compositions of the present invention may be prepared using a mineral water, for example mineral water that has been naturally mineralized such as Evian® Mineral Water (Evian, France). In one embodiment, the mineral water has a mineralization of at least about 200 mg/L (e.g., from about 300 mg/L to about 1000 mg/L). In one embodiment, the mineral water contains at least about 10 mg/L of calcium and/or at least about 5 mg/L of magnesium.

Other Materials

Various other materials may also be present in the compositions useful in the subject invention. These include humectants, proteins and polypeptides, preservatives and an alkaline agent. Examples of such agents are disclosed in the ICI Handbook, pp. 1650-1667.

The compositions of the present invention may also contain chelating agents (e.g., EDTA) and preservatives (e.g., parabens). Examples of suitable preservatives and chelating agents are listed in pp. 1626 and 1654-55 of the ICI Handbook. In addition, the compositions useful herein can contain conventional cosmetic adjuvants, such as colorants such as dyes and pigments, opacifiers (e.g., titanium dioxide), and fragrances.

The composition and products containing such compositions of this invention may be prepared using methodology that is well known by an artisan of ordinary skill.

EXAMPLES

This invention will be further illustrated below by way of Examples, but this invention is not limited thereto.

Example 1

Preparation of Compounds D, G, and F

FIGS. 1-3 illustrates the synthesis of compounds D, G, and F, respectively. For each compound, about 80-120 mg were prepared in about 95% purity.

Example 2

Formulations

Tables 1 and 2 illustrate the typical formulations of this invention. The formulation in Table 1 can be prepared by the following steps:

Aqueous Phase:
   Pour an appropriate amount of Water and start to heat up to 75° C.-80° C.,
   At room temperature add the Glycerin/Xanthan Gum premix
   At 60° C. add the Methyl Paraben and Phenoxyethanol Oily Phase:
   Add each ingredient (from Polysorbate 60 to Butyrospermum Parkii) one by one and wait for complete dissolution,
   Heat until 80° C.

Emulsification:
   When both phases reach the appropriate temperature make the emulsion by adding the oil phase to the water phase
   Mix for 20 minutes
   Decrease the temperature Cooling Phase:
   At 40° C. add the Compound G followed by the fragrance.

TABLE 1

| Ingredient Name INCI | Percentage (%) |
|---|---|
| Aqua | 69.60 |
| Methylparaben | 0.250 |
| Phenoxyethanol | 0.700 |
| Glycerin | 5.000 |
| Xanthan Gum | 0.200 |
| Aqua, Polysorbate 60, Squalane, Sodium Acryloyldimethyl Taurate/Hydroxyethylacrylate Copolymer | 1.600 |
| Glyceryl Stearate, PEG-100 Stearate | 4.000 |
| Steareth-10 | 1.400 |
| Ceteareth-20, Stearyl Alcohol | 3.000 |
| Ceteareth-20, Cetearyl Alcohol | 3.000 |
| Octyl Hydroxystearate | 3.000 |
| Isodecyl Neopentanoate | 3.000 |
| Propylparaben | 0.150 |
| Dimethicone | 3.000 |

TABLE 1-continued

| Ingredient Name INCI | Percentage (%) |
|---|---|
| *Butyrospermum Parkii* | 2.000 |
| Compound G | 0.100 |
| Total | 100.0 |

The formulation in Table 2 can be prepared by the following steps:

Aqueous Phase:
   Disperse the Carbomer in water and start to heat up to 75° C.-80° C.
   Prepare the Sodium Hydroxide solution
   Neutralize the Carbomer
   At 60° C. add the Parabens and Phenoxyethanol Oily Phase:
   Add each ingredient one (from Glyceryl Stearate to Isononyl Isononanoate) by one and wait for complete dissolution
   Heat until 80° C.

Emulsification:
   When both phase reach the right temperature make the emulsion by adding the oil phase to the Water phase
   Mix for 20 minutes
   Decrease the temperature Cooling Phase:
   At 40° C. add the Compound G followed by the fragrance

TABLE 2

| Ingredient Name INCI | Percentage (%) |
|---|---|
| Aqua | 83.55 |
| Carbomer | 0.400 |
| Methyl Paraben | 0.200 |
| Propyl Paraben | 0.150 |
| Phenoxyethanol | 0.500 |
| Sodium Hydroxide | 0.100 |
| Glyceryl Stearate, PEG-100 Stearate | 2.000 |
| Mineral Oil | 7.000 |
| Cetyl Alcohol | 1.000 |
| Isononyl Isononanoate | 5.000 |
| Compound G | 0.100 |
| Total | 100.0 |

Example 3

Test of Compound G on Human Keratinocyte Cell Line: Effects on HB-EGF and IL8 48 h after Application Compound G was tested on Human Squamous Carcinoma Cells for its ability to induce epidermal proliferation factor HB-EGF. The results are illustrated in Table 3. For this assay, Human squamous carcinoma cells were seeded in 25 cm$^2$ flask and cultivated until 80% of cell confluence was reached. Test compounds were added to the culture medium and cells were incubated again 48 hours. At the end of the incubation cells were trypsinized and pelleted. NA was extracted and gene expression was measured with quantitative real time Polymerase Chain Reaction (QRT-PCR) using actin gene expression as internal standard. Variation of gene expression is expressed in percent versus the untreated control. Effect of Compound G on HB-EGF gene expression, assessed by real time QPCR was +187% and +370% vs. control at doses of $10^{-6}$ and $10^{-5}$ M respectively. Compound G at this dose did not significantly induce IL8 expression.

TABLE 3

| Conc. of compound G | Effect on HB EGF expression vs control(48 h) | Effect on IL8 expression (48 h)vs control |
| --- | --- | --- |
| $10^{-6}$ M | 187% | 10% |
| $10^{-5}$ M | 370% | 44% |

Example 4

Effect of Compound G on Cell Proliferation after 5 Days of Application and Epidermal Thickening in Ex Vivo Human Skin Explant Ex vivo skin explants were prepared from skin abdominal biopsy after plastic surgery. Skin explants were maintained in culture medium at 37° C. in a water saturated atmosphere for 5 days. Compounds G was diluted in a mixture of propylene glycol (30%) and ethanol (70%) at 10-3 M and topically applied on the explant surface. After 48 hours, half of the explants were taken and epidermal mRNA was extracted and expression of HB-EGF and IL8 genes was measured by Quantitative real time PCR (QRT-PCR). The results are illustrated in Table 4. Explants were also fixed and slices were prepared and mounted on glass slides to be examined. Cell proliferation was also assessed by staining the cells with an antibody directed to the Ki67 protein and then counting the number of positive cell per mm (Table 4).

TABLE 4

| Conc. of compound G | Effect on HB EGF expression (48 h) vs vehicle | Effect on IL8 expression (48h)vs vehicle |
| --- | --- | --- |
| $10^{-4}$ M | 159% | 65% |
| $10^{-3}$ M | 288% | 76% |

After 5 days, of application the other half of the explants was fixed and slices were prepared and mounted on glass slides to be examined. Epidermal thickness was assessed by examination after staining by Trichrome Masson method. The results are illustrated in FIG. 4 and Table 5.

TABLE 5

| Test product | Cell proliferation (Ki67 + cells) | Epidermis thickening |
| --- | --- | --- |
| Control | 90 | + |
| Vehicle | 45 | + |
| Compound G ($10^{-3}$ M) | 150 | +++ |

We claim:

1. A compound of Formula (I)

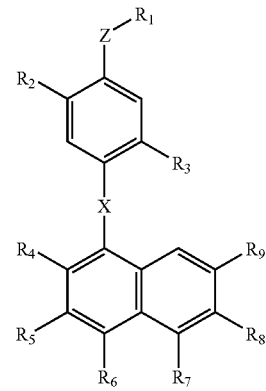

wherein
 $R_1$ is $COOR_{10}$;
 Z is selected from a bond, and O—$C_{1-4}$alkyl;
 $R_2$ is hydrogen;
 $R_3$ is hydroxyl;
 X is selected from the group consisting of —CH=CH— and —N=N—;
 $R_4$ is selected from the group consisting of hydroxy and —$NR_{15}R_{16}$;
 $R_5$ is selected from the group consisting of hydrogen and —$NR_{15}R_{16}$;
 $R_6$ is hydrogen;
 $R_7$ is hydrogen;
 $R_8$ is selected from the group consisting of hydrogen, and halo;
 $R_9$ is selected hydroxy;
 $R_{10}$ is hydrogen;
 $R_{15}$ and $R_{16}$ are each independently hydrogen; or
 a pharmaceutically acceptable or a cosmetically acceptable salt thereof.

2. The compound of claim 1, wherein $R_5$ is hydrogen.

3. A compound selected from the group consisting of

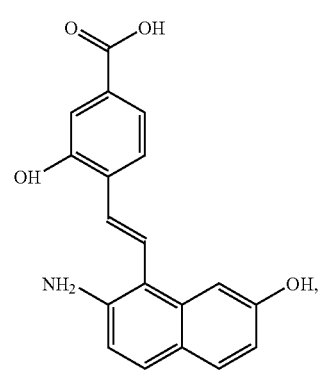

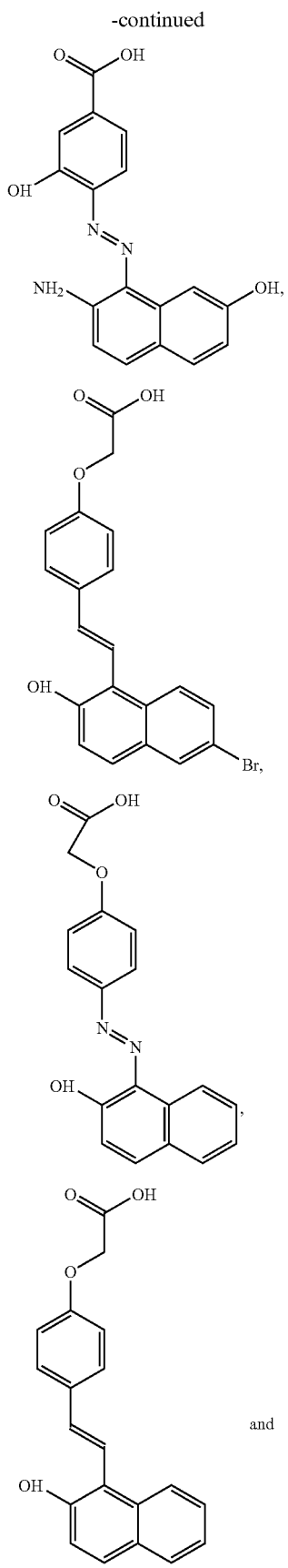

4. A cosmetic or pharmaceutical composition comprising at least one compound as claimed in claim 1.

5. A composition according to claim 4, wherein said composition comprises from 0.001% to 10% by weight of a compound as claimed in claim 1.

6. A process for preparing a composition according to claim 4, wherein the compound of Formula (I) is intimately mixed with the other constituents of the composition.

7. The compound as claimed in claim 1 for treating acne.

8. The compound as claimed in claim 1 for treating skin atrophy.

9. The compound as claimed in claim 1 for treating photoaging.

10. The compound as claimed in claim 1 for treating the skin in need of reducing the appearance of wrinkles, fine lines, stretch marks, or cellulite.

11. A compound of the formula wherein
R$^1$ is COOH;
Z is oxygen;
R2, R3, R4, R5, R6, R7, R8 and R9 are each independently H; and
X is —CH═CH—; or
a pharmaceutically acceptable or a cosmetically acceptable salt thereof.

* * * * *